(12) United States Patent
Menjoge et al.

(10) Patent No.: US 7,294,347 B2
(45) Date of Patent: Nov. 13, 2007

(54) COATING COMPOSITIONS FOR BITTERNESS INHIBITION

(75) Inventors: Anupa R. Menjoge, Maharashtra (IN); Mohan G. Kulkarni, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 401 days.

(21) Appl. No.: 10/871,534

(22) Filed: Jun. 21, 2004

(65) Prior Publication Data

US 2005/0281874 A1    Dec. 22, 2005

(51) Int. Cl.
*A61K 9/24* (2006.01)
*A61K 9/14* (2006.01)

(52) U.S. Cl. .................. 424/472; 424/487
(58) Field of Classification Search ........... 424/483, 424/487, 472
See application file for complete search history.

(56) References Cited

U.S. PATENT DOCUMENTS

| | | | | |
|---|---|---|---|---|
| 3,608,063 | A * | 9/1971 | Banker | 424/485 |
| 4,786,508 | A * | 11/1988 | Ghebre-Sellassie et al. | 424/482 |
| 5,116,603 | A * | 5/1992 | Friedman | 424/53 |
| 6,372,259 | B1 * | 4/2002 | Kumar | 424/497 |
| 6,797,768 | B2 * | 9/2004 | Lyons | 524/561 |
| 2002/0119195 | A1 | 8/2002 | Sen et al. | |
| 2003/0064108 | A1 * | 4/2003 | Lukas et al. | 424/495 |
| 2005/0136114 | A1 * | 6/2005 | Kulkarni et al. | 424/486 |
| 2005/0136115 | A1 | 6/2005 | Kulkarni et al. | |
| 2005/0137372 | A1 * | 6/2005 | Kulkarni et al. | 526/319 |
| 2005/0281874 | A1 * | 12/2005 | Menjoge et al. | 424/472 |
| 2006/0134054 | A1 * | 6/2006 | Kulkarni et al. | 424/70.16 |
| 2006/0141053 | A1 * | 6/2006 | Menjoge et al. | 424/490 |
| 2007/0072996 | A1 | 3/2007 | Kedar et al. | |
| 2007/0073014 | A1 | 3/2007 | Kedar et al. | |
| 2007/0122375 | A1 | 5/2007 | Gore et al. | |

OTHER PUBLICATIONS

Ali Said "Radiation synthesis of interpolymer polyelectrolyte complex and its application as a carrier for colon-specific drug delivery system" Biomaterials 26:2733-2739 (2005).

Moustafine et al. "Characteristics of interpolyelectrolyte complexes of Eudragit E 100 with sodium alginate" Int'l. J. Pharma. 294:113-120 (2005).

Moustafine et al. "Characteristics of interpolyelectrolyte complexes of Eudragit E100 with Eudragit L100" J. Controlled Release 103:191-198 (2005).

* cited by examiner

*Primary Examiner*—Sharon E. Kennedy
(74) *Attorney, Agent, or Firm*—Nixon & Vanderhye P.C.

(57) ABSTRACT

The present invention discloses coating compositions with taste masking property, comprising a blend of pH sensitive polymers and optionally a pH independent polymer or a blend of the pH sensitive polymer and pH independent polymer used for taste masking of highly bitter drugs. The pH sensitive polymers used comprise the acid soluble polymers and the enteric polymers. The process for the preparation of taste masked pharmaceutical compositions of the bitter drugs comprising the said coating compositions is disclosed. The concomitant use of the polymers inhibits the release of the bitter drug at the pH of saliva. The said coating compositions deliver substantial amount of the bitter drug immediately with improved palatability.

31 Claims, No Drawings

COATING COMPOSITIONS FOR BITTERNESS INHIBITION

FIELD OF INVENTION

The present invention relates to the coating compositions used for the taste masking of bitter drugs. More particularly it relates to the said coating composition comprising a blend of pH sensitive polymers in combination, and optionally pH independent polymers or a blend of the pH sensitive polymers and pH independent polymers. The present invention also relates to a process for the preparation of taste masked pharmaceutical compositions of bitter drugs comprising the coating composition of pH sensitive polymers and pH independent polymers.

BACKGROUND OF INVENTION

Although a variety of delivery systems are being developed for different routes of administration like the oral, parenteral, nasal and transdermal, the oral route remains attractive for drug delivery because this mode of administration is an easy, convenient, noninvasive and familiar method of drug delivery. The majority of prescribed drugs are designed for oral application since they can be self-administered by the patient without hospitalization. Oral dosage forms are designed according to the nature of the drug, the nature of application and the need for any special effects. The common oral dosage forms include: liquid mixtures like solutions, suspensions, solid dosage forms like tablets and capsules and liquid filled capsules etc. The solid dosage forms are further modified depending on the therapeutic action desired, like controlled, extended or delayed release. However, patients at the extremes of age, such as children and the elderly, often experience difficulty in swallowing solid oral dosages forms. For these patients the drugs are mostly provided in liquid dosage forms such as solutions, emulsions and suspensions. These dosage forms usually lead to perceptible exposure of the active drug ingredient to the taste buds, which is a very serious problem when the drug has an extremely unpleasant or bitter taste.

The bitter taste of the drugs, which are orally administered, is disadvantageous in several aspects. Taste is an important parameter governing the compliance. The disagreeable taste of drugs causes difficulties in swallowing or causes patients to avoid their medication thereby resulting in low compliance of patients. Conventional taste masking techniques such as use of sweeteners, amino acids, flavoring agents are often unsuccessful in masking the taste of the highly bitter drugs like quinine, barberin, etoricoxib, antibiotics like levofloxacin, ofloxacin, sparfloxacin, ciprofloxacin, cefuroxime axetil, erythromycin and clarithromycin. Thus taste-masking technologies are considered important and developed by many researchers.

Taste masking is a major problem when the drugs are extremely unpleasant and bitter and this problem is not restricted to the liquid oral compositions like solutions, dry syrup and suspensions but may also be encountered during the formulation of chewable tablets or dispersible tablets wherein these dosage forms usually lead to perceptible exposure of active ingredient to taste buds. Depending on the type of dosage form, various methods have been employed to overcome the unpleasant taste and bitterness of the drug.

Many polymers are employed for the taste masking of drugs. These polymers include the use of the cellulose derivatives like cellulose esters either enteric or nonenteric and cellulose ethers. The examples of the nonenteric cellulose esters include the cellulose acetate, cellulose triacetate, cellulose acetate butyrate and cellulose propionate. The enteric cellulose esters include cellulose acetate phthalate and hydroxy propyl methylcellulose phthalate. The cellulose ethers available are methylcellulose, ethyl cellulose, hydroxy ethyl cellulose, hydroxy propyl cellulose and hydroxy propyl methylcellulose. The Surelease by Dow Chemicals, and Aquacoats of FMC containing the ethylcellulose are most widely used.

A variety of polymethacrylates and acrylic polymers are available under the trade name Eudragit from Rohm Pharma. The acrylic polymers commonly employed are copolymers of methacrylic acid.

Various methods for taste masking have been tried earlier, which include use of ion exchange resins, complexation of bitter drugs with pharmaceutically acceptable excipients and coating of drugs by lipids and various polymeric materials. Of these, the coating is the most widely used technique for taste masking. Coating of the active ingredient can be done by any of the techniques known in the art like microencapsulation, hot melt granulation, Fluid bed coating, and spray drying.

European Patent EP 1219291 discloses chewable tablets and texture masked particles of the active ingredient, acetaminophen which is coated by a taste masking polymer ethyl cellulose and a film forming polymer and a texture masking coating solution of hydroxypropyl methyl cellulose and polyethylene glycol 800 and acesulfame potassium.

In another patent application JP 2002363066 the taste masked pharmaceutical or food composition is disclosed which is suitable for formulation as granule, tablet or a chewable tablet. The taste masked fine granule is obtained by using polymers such as ethyl cellulose, hydroxy propyl cellulose.

European patent EP 1166777 discloses yet another chewable tablet made from taste-masked particles. The active ingredient ibuprofen, was coated by the enteric polymer HPMCP and an insoluble film forming agent cellulose acetate and the chewable tablets which suppress throat burn were prepared from the coated particles by blending with aspartame, acesulfame potassium, citric acid, granular mannitol, fumaric acid, microcrystalline cellulose, and flavor.

Taste masking techniques are extended to the dispersible dosage forms and rapidly disintegrating tablets, too. The patent application WO 01/58449 discloses the water dispersible powder and tablets of paroxetine for the immediate release of the drug and a taste-masking agent comprising of the methacrylic acid copolymer. The taste-masked composition was obtained by spray drying of paroxetine and the polymer.

Patent Application WO 01/52848 discloses a taste masked oral formulation of linezolid which can be formulated as a suspension, a fast-disintegrating, effervescent or chewable tablet, by microencapsulating the antibiotic by solvent coacervation of ethyl cellulose with an optional seal coat of shellac and further coating the particles by functional polymer Eudragit L30 D. The formulated microcapsules can be suspended in an aqueous medium prior to oral administration to pediatric and geriatric patients, who are unwilling and/or find it difficult to swallow the tablets, else, fast-disintegrating tablets can be formulated which rapidly disperse into taste masked granules in the mouth.

The U.S. Pat. No. 6,663,893 discloses a taste masked drug with the coating composition comprising of dimethylaminoethyl methacrylate and neutral methacrylic acid ester, a cellulose ester polymer, and an alkaline modifier. The coating composition has a blend of polymer and an alkaline modifier where the alkaline modifier is added in an amount sufficient to increase the coating composition's dissolution rate in the stomach.

U.S. Pat. No. 6,001,392 discloses a controlled release syrup suspension for the oral administration containing dextromethorphan adsorbed on to a polystyrene sulfonate ion exchange resin. The drug polymer complex is coated by a mixture of ethyl cellulose or ethyl cellulose latexes with plasticizers and water dispersible polymers such as SURELEASE. For the drugs where immediate release is required for rapid action, the controlled release of the active ingredient may not be favored and a delay in release may also be of concern for drugs having a limited absorption window.

The patent application JP 2004010611 discloses the taste masking of drugs using composition of polymer containing calcium silicate, hydroxypropyl methyl cellulose acetate succinate and ethyl acrylate-methyl methacrylate copolymer.

The patent application US20040030033 discloses a film coating composition containing an acrylic polymer, a vinyl acetate polymer and a water-containing liquid. The film coat disclosed is suitable to provide modified release in pharmaceutical formulations.

The taste masked dosage forms consisting of the one or more cationic polymers synthesized from the dimethylaminoethyl methacrylate and neutral methacrylic acid esters like Eudragit E 100 and Eudragit E PO having the drug to polymer ratio less than one to two is disclosed in the patent application WO 2004022037.

Complexation is yet another method for taste masking of bitter drugs. U.S. Pat. No. 4,808,411 discloses a taste masked composition comprising 75-95% of erythromycin and about 5 to 75% of carbomer where the drug and carbomer are held together by ionic interactions between erythromycin and carbomer. The complex is further coated with a functional polymer, hydroxy propyl methylcellulose phthalate to make the preparation palatable. Erythromycin is released slowly from the complex to avoid a significant perception of bitterness in the mouth. It is clear that slow release, not fast release of bitter medicament is critical as disclosed in the patent. But complexing alone is not sufficient enough to mask taste. Coating with functional polymers is required to attain desired palatability and further proper selection of complexing agent is vital since drug release should not be compromised.

Patent Application WO 02/092106 discloses a taste-masked composition comprising polycarbophil and a macrolide antibiotic, clarithromycin. The complex is further coated with an acid resistant polymer Eudragit L100 55, releasing the drug in the intestine. For certain drugs the bioavailability may not be altered by the use of enteric coating where the drug is released in the small intestine, but for the drugs with a narrow absorption window restricted to the upper gastric region, the use of enteric coating may alter the bioavailability.

European Patent Application EP 0409254 discloses an oral particulate preparation with unpleasant taste being masked using ethyl cellulose and a water-swelling agent where the active is released rapidly from the said formulation.

U.S. Pat. No. 5,635,200 discloses a taste-masked preparation of bitter drug ranitidine by a lipid coating and dispersion of these coated particles in the non-aqueous medium. U.S. Patent Application 2003-028025 discloses taste-masked composition of gatifloxacin suitable for use in oral dosage forms, particularly for pediatric formulations. A crystalline co-precipitate of gatifloxacin and one or both of stearic acid and palmitic acid is used to effectively mask the bitter taste of gatifloxacin in the mouth and in aqueous suspension through a fill dosage cycle of fourteen days.

Patent Application WO 02/72111 discloses a taste masked pharmaceutical suspension of telithromycin. Four different coating agents Novata AB, Eudragit E100, glycerol monostearate and talc M10 are employed and at least three successive layers of coating are essential to taste mask telithromycin. The coated granules as disclosed could further be formulated as dry syrup, which is reconstituted as a suspension.

U.S. Pat. No. 4,865,851 discloses yet another method for taste masking highly bitter 1 acetoxy ethyl ester of cefuroxime in particulate form being coated with an integral coating of lipid at a mixture of lipids, which serves to mask the taste.

U.S. Pat. No. 5,286,489 describes a porous drug polymer matrix formed by admixing a bitter tasting active ingredient and a methacrylic ester copolymer in at least a 1:1 weight ratio of active ingredient to copolymer, effective to mask the taste of the drug. None of the examples described in the patent disclose the effect of these polymers on the release of the drug from the matrix. It is observed that the drug release is retarded from the matrix described herein.

Patent Application WO 00/56266 discloses the use of a high viscosity swellable polymer carbomer, in combination with film forming polymethacrylates and channelising agents for taste masking of bitter drugs. The addition of the water swellable polymer aids in the fast release of the active ingredient in the gastric media.

In yet another Patent application WO 00/76479 a taste masking composition, using a combination of two enteric polymers comprising methacrylic acid copolymer and a phthalate polymer is disclosed. The patent discloses the use of the channelising agents, which comprise the water-soluble or water swellable materials to aid the release of the active ingredient. The enteric polymers as disclosed in the patent are known to release the active ingredient in the alkaline pH where the polymers are soluble. Release of active ingredient will be delayed due to the use of the enteric polymers and in case of the medicaments having a narrow absorption window restricted to upper gastrointestinal tract, such system would be of limited use.

The taste masking formulations should be so designed that the bioavailability of the drugs is not compromised and the use of certain polymers like the enteric coatings should not affect the time to peak. Further the drug should be sufficiently absorbed to ensure effective therapeutic concentration in the plasma. Vogelman et al (B. Vogelman, William A. Craig Journal of Pediatric 1986, 108 (5, pt2) 835-40, & B. Vogelman, William A. Craig, S. Ebert, S. Gudmundsson, J. Leggett, Journal of Infectious Diseases 1988, 158(4), 831-47) have established that bactericidal killing is rapid, intensive and increases proportionately to the concentration. In the presence of high concentration of the drug, the killing is complete and almost instantaneous. In some drugs rapid and complete absorption and high systemic concentration are important to elicit the desired therapeutic effect.

Patent Application WO 02/43707 discloses oral pharmaceutical formulations for cefuroxime axetil in tablet form such that the cefuroxime axetil is contained in the tablet core, coated with double layered film coat of hydroxypropyl methyl cellulose and shellac. The first film coat as disclosed, serves to mask bitter taste of cefuroxime axetil and second film coat serves to delay the rupture time beyond 40 seconds.

Since cefuroxime axetil is associated with gelling tendency in contact with aqueous media thereby reducing bioavailability, the rapid release of cefuroxime axetil from the core of the dosage form is more desirable.

U.S. Pat. No. 5,599,556, discloses liquid formulations where the active ingredient is coated with single outer polymeric coating derived from prolamine cereal grain proteins and plasticizing agent. The bitter drug clarithromycin comixed with polyvinyl pyrrolidone is coated by prolamine to achieve taste masking and the coated particulate matter is dispersed in a suspending medium of pH greater than 6. The coatings are designed to rapidly degrade once the composition leaves the mouth and reaches the stomach.

U.S. Pat. No. 548,436 discloses chewable tablets made from a coated medicament where the coating is designed to be soluble at the lower pH of the stomach but relatively water insoluble at the higher pH of the mouth. The coatings comprise a polymer blend of dimethylamiaoethyl methacrylate and neutral methacrylic acid ester and a cellulose ester. The above mentioned "reverse enteric" coating method of taste masking oral formulation is disclosed in connection with chewable tablets.

Patent Application WO 02/096392 discloses taste masking of highly water soluble drug cetrizine hydrochloride. The polymers like hydroxy propyl methyl cellulose, polyvinyl pyrrolidone, ethyl cellulose are used which effectively mask the taste of cetrizine in tablet form and release the drug immediately under the acidic conditions prevalent in stomach.

It is evident from the above disclosures, that taste masking can be achieved by various methods. Many natural and synthetic polymers, resins and waxes alone or in combination have been employed for taste masking. Whilst the use of polymer coats as mentioned in the above examples may be effective for taste masking, they retard dissolution of the drug. It is understood that there is a need for the development of such coating compositions, which are suitable for the application in the solid dosage forms and also the liquid orals. The maintenance of palatability of the formulations in the liquid dosage forms is more critical as here the possibility of the leaching of the drug in the surrounding media is more. A higher amount of the polymers may be required to achieve this. However as the amount of the enteric or the pH independent polymers like the ethyl cellulose is increased, there is a possibility of the retardation of the drug release. Hence there is a need to design the polymeric coating compositions, which are effective in taste masking, retarding the drug release in the aqueous media and yet releasing substantial amount of the drug without delay. The coating compositions should be such that they release the drug almost completely from the dosage form without affecting its absorption and bioavailability.

The present invention addresses this problem by incorporation of an acid soluble polymer in combination with other polymers, either pH independent or pH dependent with a specific dissolution window in the acidic pH<3.

The polymeric coating compositions disclosed it the present invention employing the combination of the pH dependent polymer like the acid soluble and the enteric polymer have the advantage that they would ensure complete release of the drug due to the presence of the acid soluble part and could be reconstituted in the pH range 3.5-5. Further the coating composition employing the acid soluble polymer and the pH independent polymers will have the advantage of the broader reconstitution pH range of 3.5 and above and yet the drug being released without much delay due to the solubilisation of the acid soluble polymer in the stomach. Further advantage is that when the polymer blends are used the total quantity of the polymer can be increased for better taste masking effect making optimal use of the properties of individual polymers constituting the blend without compromising the release.

OBJECTS OF THE INVENTION

The object of the present invention is to use the blend of pH dependent polymers in varying combinations, either alone or in combination with pH independent polymers or a blend of the pH sensitive polymer and pH independent polymer to mask the bitterness of pharmaceutical compositions comprising extremely bitter drugs. The said coating compositions deliver substantial amount of the bitter drug immediately with improved palatability.

The object of the present invention is to develop the coating compositions, which can be used for the taste masking of the bitter drugs, more importantly the coating compositions are aimed at the rapid release of the drug on ingestion and thus the availability of the drugs is not altered. Further the coating composition does not release the drug at the pH of the saliva and also in the reconstitution medium in liquid orals.

The other object of the present invention is to essentially use the specially synthesized pH sensitive polymers, which solubilize or swell at the acidic pH of the stomach but are insoluble at the near neutral or neutral pH. The composition and method of preparation are disclosed in our earlier filed patent applications PCT/IN03/00390 and PCT/IN03/00392.

Further the object of the present invention is to use the pH dependent polymers comprising essentially of the acid soluble or acid swellable polymer in combination with the other pH sensitive polymers comprising of the enteric polymers and optionally of the pH independent polymers.

Another object of the present invention is to use the acid soluble or swellable polymer in combination with an enteric polymer or a combination of the enteric polymers.

Yet another object of the present invention is to use the acid soluble or swellable polymer in combination with the pH independent polymer for masking bitterness.

Yet another object of the present invention is to describe the use of combination of the pH sensitive polymers and optionally the pH independent polymers in the taste masked pharmaceutical composition and the method of preparation thereof Yet another object of the present invention is to develop taste masked particles which can be used in liquid orals like suspensions, dry syrups, and solid dosage form like chewable tablets, fast dispersible tablets and conventional tablets.

A further object of the present invention is to prevent leaching of the drug at the pH of saliva from the liquid and solid dosage forms.

The present invention also aims at the coating of the bitter drug particle by various methods known in the art like microencapsulation, tray drying, fluid bed processing and spray drying etc.

SUMMARY OF THE INVENTION

Accordingly the present invention relates to a coating composition for the taste masking of pharmaceutical compositions containing a bitter drug, wherein the said coating composition comprises an acid soluble or swellable polymer in combination with one or more enteric coating polymers as pH dependent polymer and/or pH independent polymers: wherein said acid soluble or swellable polymer has a formula: P[A$_{(x)}$B$_{(y)}$C$_{(z)}$] wherein P is polymer comprising (A) a hydrophobic monomer, (B) a basic monomer and (C) a hydrophilic monomer where, (x)=30-95%,(y)=5-70%,(z)=0-60%, all expressed in terms of w/w such that x+y+z=100%.

The acid soluble or swellable polymer in coating composition comprises of methyl methacrylate, hydroxy ethyl methacrylate and vinyl pyridine in the range of 50-75%, 15-35% and 5-15% w/w respectively.

In one of the embodiments of the present invention the coating composition comprises essentially of polymeric blends wherein one of the polymer is acid soluble or swellable polymer.

In another embodiment the coating composition used for the taste masking comprises the blend of acid soluble or swellable polymer and the enteric polymer.

In yet other embodiment of the present invention the coating composition used for the taste masking comprises the blend of acid soluble or swellable polymer, enteric and pH independent polymer.

In yet another embodiment of the present invention the coating composition used for the taste masking comprises the blend of acid soluble or swellable polymer and pH independent polymers.

The embodiment of the present invention which comprises essentially acid soluble or swellable polymer in coating composition wherein the monomer composition of the said polymer is methyl methacrylate, hydroxy ethyl methacrylate and vinyl pyridine in the range 50-75%, 15-35% and 5-15% w/w respectively.

In yet another embodiment of the invention, the coating composition comprises blend of pH dependent polymer, wherein the other polymer is selected from the group consisting of enteric polymers like the cellulosic esters viz cellulose acetate phthalate, hydroxymethyl cellulose phthalate, cellulose trimellitate, hydroxymethyl cellulose acetate succinate, resins like shellac and polymethacrylates viz copolymers of methylmethacrylate-methacrylic acid and, methacrylic acid-ethyl acrylate. The pH independent polymers are cellulosic ethers such as ethyl cellulose, methyl cellulose, hydroxy ethyl cellulose, hydroxy propyl cellulose, hydroxy propyl methyl cellulose, carboxy methyl cellulose, and proteins like prolamine, zein.

In the embodiment of the present invention the coating composition used in taste masked composition has a ratio of the acid soluble or swellable polymer to enteric polymer, in the range 1:0.1 to 1:5.

Further in the embodiment of the present invention the coating composition used in taste masked composition has a ratio of pH dependent polymer to pH independent polymer, in the range 1:0.05 to 1:5.

In yet another embodiment of the present invention a pharmaceutical composition comprising a coating composition and macrolide antibiotic drug is selected from the group consisting of erythromycin, azithromycin and clarithromycin, fluroquinolones selected from the group consisting of ciprofloxacin, enrofloxacin, ofloxacin, gatifloxacin, levofloxacin and norfloxacin, cephalosporins selected from the group consisting of cefuroxime, cephalexin, cephadroxil, cepfodoxime proxetil, nonsteoroidal, and anti-inflammatory and analgesic drugs selected from the group consisting of ibuprofen and diclofenac sodium; and COX 2 inhibitors selected from the group consisting of etoricoxib and celecoxib; antibistamic drugs selected from the group consisting of chlorpheniramine maleate, oxazolidinones selected from the group consisting of linezolid and other drug like dextromethorphan.

In the embodiment of the present invention the coating composition used in taste masked composition has the ratio of acid soluble or swellable polymer to pH independent polymer as 1:0.1 to 1:5.

In another embodiment of the present invention the pharmaceutical composition comprises a drug or its pharmaceutically acceptable salt or ester or amide and the polymer coating composition wherein the drug is a macrolide antibiotic selected from the group consisting of erythromycin, azithromycin and clarithromycin, fluroquinolones selected from the group consisting of ciprofloxacin, enrofloxacin, ofloxacin, gatifloxacin, levofloxacin and norfloxacin, cephalosporins selected from the group consisting of cefuroxime, cephalexin, cephadroxil, cepfodoxime proxetil, nonsteoroidal, and anti-inflammatory and analgesic drugs selected from the group consisting of ibuprofen and diclofenac sodium and COX 2 inhibitors selected from the group consisting of etoricoxib and celecoxib, antihistamic drugs selected from the group consisting of chlorpheniramine maleate, oxazolidinones selected from the group consisting of linezolid and other drug like dextromethorphan.

In yet other embodiment of the present invention the total polymer to drug ratio in the pharmaceutical composition is in the range 0.1:1 to 4:1 by weight.

In another embodiment of the invention the composition comprises drug in the form of the microparticles, either dispersed within polymer matrix or coated by the polymer.

The pharmaceutical composition as disclosed comprises the microparticles, which can be formulated in a pharmaceutically acceptable dosage form. The pharmaceutical composition does not release drug at pH of saliva from the oral dosage form but rapidly releases substantial amount of the drug immediately at pH≦3 found in the stomach. The pharmaceutical composition can be formulated as liquid orals comprising dry syrup and suspension or as solid dosage form like chewable, effervescent, rapidly disintegrating or dispersible tablets.

Accordingly the pharmaceutical composition is obtained by dispersion or coating of the bitter drug in the matrix of coating composition of polymers by any of the known techniques like microencapsulation, spray drying, fluid bed processing, co precipitation in a non solvent or by tray drying method. The taste masked composition in particulate form as of the present invention comprising the blend of acid soluble or swellable polymer and the enteric polymer can be suspended using the reconstitution medium of pH 3.5 to 5.

The taste masked coated composition in the particulate form comprising the blend of acid soluble or swellable polymer, enteric and pH independent polymer can be suspended using the reconstitution medium of pH 3.5 to 5.

The taste masked coated composition in particulate form comprises of the blend of acid soluble or swellable polymer and pH independent polymer and can be suspended in reconstitution medium of pH>3.5. The pharmaceutical composition comprises the drug itself or its pharmaceutically acceptable salt or an ester or an amide.

Accordingly, in the present invention the process for preparation of drug microparticles is by microencapsulation using an emulsification solvent evaporation method comprising dissolving the polymer constituting the polymer blend in an organic solvent selected from acetone, methanol, dichloromethane and a mixture of methanol and dichloromethane in the ratio 1:1 to 1:1.5, or a mixture of acetone and methanol in the ratio 1:1 or a mixture of acetone methanol and dichloromethane in the ratio 1:1:0.1, adding the drug to the polymer solution to obtain a solution or a dispersion, adding this organic phase to light liquid paraffin-containing span 85 in an amount of 0.1 to 1% w/w, continuously stirring the mixture mechanically at a rate of about 500-1000 rpm and at a temperature of about 25° C. for a period of about 3-5 hrs and then separating the microparticles by filtration and washing the separated microparticles with petroleum ether or n hexane and drying at a temperature of about 27° C. under vacuum for up to 24 hours.

Accordingly the coating compositions of the present invention provide the taste masked pharmaceutical compositions which do not release the drug in the saliva and which release the drug without any delay at the pH of stomach and the coating compositions are not soluble in water. Further the increase in the polymeric coating does not alter the release and provides better protection in the reconstitution medium.

DETAILED DESCRIPTION OF THE INVENTION

Mostly medicaments are administered via the oral route for the ease and convenience of the patients. The disadvantage of this is that in certain dosage forms where the drug is extremely bitter, it causes discomfort and the compliance of the patients is adversely affected. This effect is profound in the case of the pediatric and geriatric patients and where the drugs are formulated as the liquid orals or other preparations like the rapidly disintegrating, dispersible or chewable tablets for ease of swallowing. The taste masking techniques are hence applied extensively to improve the palatability of the dosage forms.

The present invention provides oral pharmaceutical compositions, which effectively mask the bitter, unpleasant and otherwise undesirable taste of the active ingredient. More specifically the invention relates to the use of the coating compositions, which mask the bitter taste of the drugs and also release a substantial amount of drug upon administration without delay.

Taste masked compositions making use of the synthetic acid soluble polymers and their applications in various pharmaceutical compositions providing substantial immediate release without causing any delay in the absorption of the active ingredient are disclosed in patent applications PCT/IN03/00390 and PCT/IN03/00392. The use of these polymers is effective in taste masking of the drugs to be used in the oral dosage forms like the liquid orals and the solid dosage forms like the chewable, dispersible, rapidly disintegrating tablets. The advantage of these polymers is that they are insoluble at the near neutral pH and are soluble at the acidic pH so that the release of the drug in the stomach is not affected. Further the polymers disclosed in these applications showed no negative interaction with the drugs as shown by the use of Eudragit E in presence of the drug Cefuroxime axetil. The polymer compositions disclosed in these applications are very useful for the taste masking of bitter drugs since they release the drug in gastric pH without any delay and prevent the leaching at the pH of saliva. The polymer compositions disclosed in these applications are very useful for taste masking of the solid dosage forms like the conventional film coated tablets, the rapidly disintegrating tablets and the chewable tablets and the dispersible tablets where the amount of the polymer required is comparatively less.

Depending on the type of dosage form the amount of the polymer required for imparting palatability will vary. Further the dose of the active ingredient will also affect the performance of the polymer coating. In some cases where the dose is higher, the amount of polymer required to provide effective coating may be more. The liquid dosage forms like dry syrup and suspensions require a more uniform and complete polymer coat to impart taste masking effect and the polymer requirement is higher as compared to the conventional solid dosage forms. In the case of the liquid dosage forms, the polymer has to provide taste masking effect by preventing leaching of the drug from the formulation during the reconstitution period. However in certain drugs, which are extremely bitter and may remain palatable for a short period but may release some of the drug later, in such a case higher loading of the polymer is required to provide the desired taste masking effect. Further during swallowing, if any particles are retained in mouth, then the polymer coating should prevent the leaching of the drug from the coated particles and also if these particles get chewed, the polymer coating should prevent the bitter taste in the mouth. Such situations are commonly found in the pediatric patients. So the amount of the polymeric coating has to be higher to impart the desired palatable characteristic.

The maximum permissible amount of a polymer in a formulation is decided on the basis of the safety and maximum potency of the polymer. This restricts the total amount of the polymer to be used in a formulation. The present invention discloses the use of the blends of the polymeric coatings such that the blend masks bitter taste of the drug and when used concomitantly the amount of the individual polymer component falls within the safe acceptable limits. The polymer blends used are such that the taste masking effect is not compromised and the amount of the polymer blend is sufficient to provide better barrier to leaching of the drug in the liquid oral preparation. Further these compositions can be used in the solid dosage forms. The advantage of using the polymer blends comprising the acid soluble or swellable polymer in conjunction with the other pH dependent polymers and the pH independent polymers is that the acid soluble polymer dissolves or swells in the acidic environment of the stomach and causes the release of the drug without delay.

The coating compositions disclosed in the patent applications PCT/IN03/00390 and PCT/IN03/00392 are very useful for the drugs which have better absorption from the stomach. However the drugs, which are absorbed all along the gastrointestinal tract, need polymeric coatings, which will release the drug even in the intestinal region. So there is a need to develop the coating compositions, which release the drug in stomach and other parts of the gastrointestinal tract. The use of the enteric polymers, delays the release till the dosage form reaches the intestine. However the coating compositions disclosed in the present invention overcome the limitation by releasing the substantial amount of drug in the gastric region and the remaining drug in the intestinal region. Further the commercially available reverse enteric polymer Eudragit E cannot be used in combination with the other enteric polymers like hydroxy propyl methylcellulose phthalate and Eudragit L as there is precipitation of polymers in presence of the organic solvents. The coating compositions containing the acid soluble or swellable polymer as disclosed in the present invention do not precipitate in presence of Eudragit L, hydroxy propyl methyl cellulose phthalate and cellulose acetate phthalate.

This type of coating composition as disclosed in the present application has advantage over the other earlier methods disclosed in prior art employing the blends of the enteric polymers or the blends of the enteric polymer and the pH independent polymers like the cellulose ethers which retards the release of the drug in the stomach. Further the coating compositions of the present invention can be used for a variety dosage forms.

One of the advantages of the coating composition used, as disclosed in the present application is that the coating composition essentially incorporates the synthetic acid soluble polymer such that it dissolves or swells thereby releasing the drug in the stomach and thus there is no delay in the drug release. The acid soluble or swellable polymer as disclosed in the application PCT/IN03/00390 and PCT/IN03/00392 has a formula $P[A_{(x)}B_{(y)}C_{(z)}]$ wherein P is the acid soluble or swellable polymer comprising (A) a hydrophobic monomer, (B) a basic monomer and (C) a hydrophilic monomer and (x)=30-95%, (y)=5-70%, (z)=0-60%, all expressed in terms of w/w such that x+y+z=100%. The acid soluble pH sensitive polymer comprises of essentially a hydrophobic monomer, a basic monomer and optionally a hydrophilic monomer.

The acid soluble or swellable polymer used in coating composition comprises of methyl methacrylate, hydroxy ethyl methacrylate and vinyl pyridine in the range of 50-75%, 15-35% and 5-15% w/w respectively.

The coating composition as disclosed in the present application comprises essentially of the acid soluble polymer as one of the polymers in the polymeric blends.

The coating composition used for the taste masking application as disclosed in the present invention comprises of the blend of acid soluble or swellable polymer and the enteric polymer or a blend of acid soluble or swellable polymer, enteric and optionally pH independent polymers or a blend of acid soluble or swellable polymer and pH independent polymers.

The pH dependent polymers in coating composition wherein the other polymer is selected from the group consisting of enteric polymers like the cellulosic esters like cellulose acetate phthalate, hydroxymethyl cellulose phthalate, cellulose trimellitate, hydroxymethyl cellulose acetate succinate, resins like shellac and polymethacrylates like copolymers of the methylmethacrylate—methacrylic acid and, methacrylic acid-ethyl acrylate preferably enteric polymers like the cellulosic esters viz cellulose acetate phthalate, hydroxymethyl cellulose phthalate reisns like shellac and polymethacrylates like copolymers of the methylmethacrylate—methacrylic acid.

The pH independent polymer in coating composition comprises cellulosic ethers like ethyl cellulose, methylcellulose, hydroxy ethyl cellulose, hydroxy propyl cellulose, hydroxy propyl methylcellulose, carboxy methylcellulose, and proteins like prolamine, zein preferably cellulosic ethers like ethyl cellulose and proteins like prolamine and zein.

The present invention also provides for the taste masking of bitter drugs like macrolide antibiotics such as erythromycin, azithromycin and clarithromycin, fluroquinolones such as ciprofloxacin, enrofloxacin, ofloxacin, gatifloxacin, levofloxacin and norfloxacin, cephalosporins such as cefuroxime, cephalexin, cephadroxil, cepfodoxime proxetil, nonsteoroidal and anti-inflammatory and analgesic drugs such as ibuprofen, diclofenac sodium and COX 2 inhibitors like etoricoxib and celecoxib, antihistamic drugs like chlorpheniramine maleate, oxazolidinones like linezolid and other drug like dextromethorphan.

The drug itself or its pharmaceutically acceptable salt or ester or amide may be used in the present invention. The drugs preferred for the practice of present invention can be chosen from a wide range comprising cefuroxime axetil, ciprofloxacin, celecoxib and clarithromycin. As a representative bitter drug the cephalosporin antibiotic cefuroxime axetil is chosen but the invention is not restricted to the drug only it can be used in relation to a wide range of the drugs which require to be taste masked.

The pharmaceutical composition described herein has the total polymer to drug ratio for optimal taste masking bitter drug in the range 0.1:1 to 4:1 by weight. More preferably the ratio of the total polymer to drug is 0.5:1 to 3:1 by weight. The coating composition used for the taste masking has a ratio of the acid soluble or swellable polymer to enteric polymer in the range of 1:0.1 to 1:5.

The coating composition used for the taste masking has a ratio of pH dependent polymer to pH independent polymer is in the range of 1:0.05 to 1:5.

The coating composition used for the taste masking has a ratio of the acid soluble or swellable polymer to pH independent polymer in the range of 1:0.1 to 1:5.

The invention comprises development of a taste masked formulation using the blend of various polymers in varying proportions, the said composition is in the form of microparticles wherein the drug is dispersed in the polymer matrix or coated by the polymer coating. The coatings are capable of masking the bitterness and maintain the palatability of the pharmaceutical composition while still providing immediate release and bioavailability upon exposure to the pH levels found in the stomach of a human.

The taste-masked particles obtained as described in the invention can be optionally blended with other pharmaceutically acceptable excipients such as flavors, sweeteners, suspending agents and or preservatives and formulated as dry syrup or compressed into fast disintegrating, effervescent or chewable tablets.

The mean particle size of the microcapsules will be in the range of about 30 to 1000 microns, most preferably in the range of up to 500 microns.

In another feature of the present invention the pharmaceutical composition may be obtained by coating the drug using pH sensitive polymer either by microencapsulation, spray drying, fluid bed processing, co-precipitation in a non solvent or by tray drying method.

In still another feature the taste masking compositions are made by microencapsulation of the drug in the polymer matrix. The microencapsulation of the bitter drugs can be obtained by emulsification, solvent evaporation or solvent traction and spray drying of the drug polymer solution or dispersion of drug in polymer solution. If the drug is not soluble in the polymer solution then it is dispersed in the polymer solution uniformly with the help of the dispersing agents like the surfactants. The preferred surfactants are the nonionic surfactants belonging to the class of SPAN and TWEEN. Preferably the solvent is selected such that the drug and the polymer are both soluble in the solvent. In another feature of the present invention the solvents chosen for the solubilization of the drug and polymer are alcohols like methanol, ethanol, isopropanol, butanol, chlorinated hydrocarbons like dichloromethane, chloroform, ketones like methyl ethyl ketone, methyl iso-butyl ketone and acetone. Preferably the solvents used to dissolve the drug and polymers are methanol, acetone and dichloromethane and a mixture of methanol and dichloromethane in the ratio 1:1 to 1:1.5, or a mixture of acetone and methanol in the ratio 1:1 or a mixture of acetone methanol and dichloromethane in the ratio 1:1:0.1

The taste-masked microcapsules of the bitter drug can be obtained by microencapsulation by emulsification solvent evaporation technique. The dispersed phase is the organic solvent containing the drug and polymer and the dispersion medium is the liquid paraffin. The polymer blend is dissolved in the organic solvent. The drug is added to the polymeric solutions resulting in a solution or a dispersion. The organic phase is then added into light liquid paraffin-containing span 85 (0.1 to 1% w/w). A constant mechanical stirring rate of 1000 rpm and at room temperature is maintained for 3-4 hours. The solvent is allowed to evaporate and the microspheres so obtained are separated by filtration, washed by petroleum ether or by n hexane and dried under vacuum for up to 24 hours.

Alternately the taste masked micro particles can be obtained by spray drying or fluid bed coating of the drug particles. The taste masked particles and granules obtained may be mixed with the flavoring agents such as natural or artificial flavors, citric and tartaric acids, sweeteners such as sucrose, saccharin and aspartame, and other pharmaceutically acceptable excipients to be formulated as conventional, chewable or dispersible tablets, dry syrups, suspensions, sachets or any other suitable oral dosage form.

The present invention is more directed towards the taste masking of the liquid oral compositions suitable for the pediatric patients or those, who have a difficulty in swallowing the solid dosage form. The taste masked pharmaceutical composition can be prepared by reconstitution of the polymer coated drug particles in a suitable liquid vehicle as described below.

A taste masked composition in particulate form wherein the coating composition comprises of the blend of acid soluble or swellable polymer and the enteric polymer can be suspended using the reconstitution medium of pH 3.5 to 5.

A taste masked composition in particulate form wherein the coating composition comprises of the blend of acid soluble or swellable polymer, enteric and pH independent polymer can be suspended using the reconstitution medium of pH 3.5 to 5.

A taste masked composition in particulate form wherein the coating composition comprises of the blend of acid soluble or swellable polymer and pH independent polymer can be suspended using the reconstitution medium of pH>3.5.

The taste masked pharmaceutical compositions as exemplified in the examples 1-7 given below were tested for the drug release with respect to time. The taste masked compositions were tested for cefuroxime axetil release in 900 ml of 0.07 N hydrochloric acid for 3 hours after which the dissolution media was changed to pH 6.8 phosphate buffer thereafter (USP apparatus type II) and were rotated at 75 rpm. The samples were withdrawn at 0.5, 1, 2, 3 and 4 hrs. The amount withdrawn each time was replaced with fresh media to maintain the sink conditions.

The coating compositions for the taste making of the bitter drugs are described herein below with reference to the examples, which are illustrative only and should not be construed to limit the scope of the present invention in any manner.

EXAMPLE 1

The acid soluble or swellable polymer was synthesized by solution polymerization. The hydrophobic monomer, basic monomer and optionally a hydrophilic monomer were dissolved in the solvent, dimethyl formamide The polymer has the monomer composition Methyl methacrylate 65% by weight Hydroxyethyl methacrylate 24% by weight and Vinyl Pyridine 11% by weight. An azo initiator, azo bis isobutyronitrile was added to the monomer solution in dimethyl formamide. The reaction mixture was purged with the nitrogen gas to provide the inert atmosphere. The polymerization reaction was carried out by heating the reaction mixture to 65° C. for a period of 18 hours. The polymer so synthesized was recovered by precipitation, in a nonsolvent. The nonsolvent water was used. The polymer was dried at 45° C. under vacuum.

EXAMPLE 2

The acid soluble or swellable polymer was synthesized by solution polymerization. The hydrophobic monomer, basic monomer and optionally a hydrophilic monomer were dissolved in the solvent, dimethyl formamide. The polymer has the monomer composition Methyl methacrylate 73% by weight Hydroxyethyl methacrylate 18% by weight and Vinyl Pyridine 9% by weight. An azo initiator, azo bis isobutyronitrile was added to the monomer solution in dimethyl formamide. The reaction mixture was purged with the nitrogen gas to provide the inert atmosphere. The polymerization reaction was carried out by heating the reaction mixture to 65° C. for a period of 18 hours. The polymer so synthesized was recovered by precipitation in a nonsolvent. The nonsolvent water was used. The polymer was dried at 45° C. under vacuum.

EXAMPLE 3

The acid soluble or swellable polymer was synthesized by solution polymerization. The hydrophobic monomer, basic monomer and optionally a hydrophilic monomer were dissolved in the solvent, dimethyl formamide. The polymer has the monomer composition Methyl methacrylate 56% by weight Hydroxyethyl methacrylate 31% by weight and Vinyl Pyridine 13% by weight. An azo initiator, azo his isobutyronitrile was added to the monomer solution in dimethyl formamide. The reaction mixture was purged with the nitrogen gas to provide the inert atmosphere. The polymerization reaction was carried out by heating the reaction mixture to 65° C. for a period of 18 hours. The polymer so synthesized was recovered by precipitation in a nonsolvent. The nonsolvent water was used. The polymer was dried at 45° C. under vacuum.

EXAMPLE 4

The taste masked compositions are made by dispersing the drug in the coating composition and obtaining the microparticles of the drug by microencapsulating the drug polymer mixture in the liquid paraffin and evaporation of the solvent. Coating composition: The coating compositions containing the various polymer blends are shown in the table 1. The acid soluble polymer prepared in example 1 is used in all coating compositions as one of the pH dependent polymer. The amount of solvent used is 7 ml of mixture of methanol and dichloromethane in the ratio 1:1 to 1:1.5, or a mixture of acetone and methanol in the ratio 1:1 or a mixture of acetone methanol and dichloromethane in the ratio 1:1: 0.1 Amount of drug to coating polymer compositions is shown in table 1 The taste masked microcapsules were obtained by emulsification solvent evaporation technique. Cefuroxime axetil was dispersed in polymer solution made with requisite amount of solvent using the desired mixture of solvents. The nonionic surfactant Span 85 was added 0.1% w/w to facilitate the dissolution and dispersion of cefuroxime axetil in the polymer solution. The polymer-drug mixture was added dropwise to the bath of light liquid paraffin under mechanical stirring. Span 85 was added to the paraffin oil 0.5% to facilitate the dispersion of the polymer drug mixture. A constant mechanical stirring rate of 500 rpm and at room temperature was maintained for a 3-4 hours. The solvent was allowed to evaporate and the microparticles so obtained were separated by filtration, washed by petroleum ether and dried at 27° C. under vacuum for 24 hours. The drug release pattern of the composition prepared was monitored and the results are tabulated in Table 2

TABLE 1

| | Polymer composition | | Drug |
|---|---|---|---|
| | pH dependent polymer | | Cefur- |
| S. No | Acid Soluble polymer | Enteric polymer | pH independent polymer | oxime axetil |
| 1 | Acid soluble polymer 0.3 g | — | zein 0.6 g | 0.6 g |
| 2 | Acid soluble polymer 0.3 g | — | zein 0.3 g, ethyl cellulose 0.33 g | 0.6 g |
| 3 | Acid soluble polymer 0.3 g | — | zein 0.15 g, ethyl cellulose 0.025 g | 0.6 g |
| 4 | Acid soluble polymer 0.3 g | — | ethyl cellulose 0.06 g | 0.6 g |
| 5 | Acid soluble polymer 0.3 g | — | ethyl cellulose 0.045 g | 0.6 g |
| 6 | Acid soluble polymer 0.3 g, | shellac 0.348 g | — | 0.6 g |
| 7 | Acid soluble polymer 0.3 g | shellac 0.12 g | Zein 0.28 g | 0.6 g |
| 8 | Acid soluble polymer 0.2 g | hydroxy propyl methylcellulose phthalate 0.2 g | — | 0.6 g |
| 9 | Acid soluble polymer 0.3 g, | hydroxy propyl methylcellulose phthalate 0.05 g | — | 0.6 g |
| 10 | Acid soluble polymer 0.2 g | Eudragit L 100 0.1 g | — | 0.6 g |
| 11 | Acid soluble polymer 0.3 g, | hydroxy propyl methyl cellulose phthalate 0.025 | Ethyl cellulose 0.015 g | 0.6 g |
| 12 | Acid soluble polymer 0.3 g | Cellulose Acetate phthalate 0.035 g | — | 0.6 g |
| 13 | Acid soluble polymer 0.2 g | Eudragit S 100 0.1 g | — | 0.6 g |
| 14 | Acid soluble polymer 0.3 g | Eudragit L 100 0.02 g Cellulose Acetate phthalate 0.02 g | | |

TABLE 2

| | | % Drug released Tame in min | | | | | |
|---|---|---|---|---|---|---|---|
| S. No | Composition | 30 | 60 | 120 | 180 | 240 | 300 |
| 1 | Acid soluble polymer 0.3 g zein 0.6 g cefuroxime axetil 0.6 g | 45.33 | 54.0 | 60.0 | 65.8 | 79.81 | — |
| 2 | Acid soluble polymer 0.3 g, zein 0.3 g, ethyl cellulose 0.33 g cefuroxime axetil 0.6 g | 40.43 | 55.0 | 69.24 | 73.62 | 84.22 | — |
| 3 | Acid soluble polymer 0.3 g zein 0.15 g, ethyl cellulose 0.025 g cefuroxime axetil 0.6 g | 47.68 | 64.17 | 75.67 | 78.57 | 85.58 | 93.0 |
| 4 | Acid soluble polymer 0.3 g ethyl cellulose 0.06 g cefuroxime axetil 0.6 g | 54.28 | 71.97 | 80.55 | 81.57 | 84.33 | — |
| 5 | Acid soluble polymer 0.3 g ethyl Cellulose 0.045 g cefuroxime axetil 0.6 g | 55.09 | 69.58 | 81.76 | 87.14 | 93.40 | — |
| 6 | Acid soluble polymer 0.3 g shellac 0.348 g cefuroxime axetil 0.6 g | 49.45 | 54.88 | 58.98 | 61.0 | 77.2 | — |
| 7 | Acid soluble polymer 0.3 g shellac 0.12 g Zein 0.28 g cefuroxime axetil 0.6 g | 52.5 | 56.0 | 64.36 | 68.8 | 78.57 | — |
| 8 | Acid soluble polymer 0.2 g hydroxy propyl methyl cellulose phthalate 0.2 g cefuroxime axetil 0.6 g | 35.05 | 47.47 | 58.09 | 63.75 | 78.23 | — |
| 9 | Acid soluble polymer 0.3 g hydroxy propyl methyl cellulose phthalate 0.05 g cefuroxime axetil 0.6 g | 52.61 | 65.34 | 76.41 | 77.17 | 86.68 | 97.22 |
| 10 | Acid soluble polymer 0.2 g Eudragit L 100 0.1 g cefuroxime axetil 0.6 g | 51.71 | 54.0 | 59.0 | 72.36 | 82.29 | — |
| 11 | Acid soluble polymer 0.3 g hydroxy propyl methyl cellulose phthalate 0.025 g Ethyl Cellulose 0.015 g cefuroxime axetil 0.6 g | 76.11 | 81.86 | 85.4 | 90.88 | 97.0 | — |
| 12 | Acid soluble polymer 0.3 g Cellulose Acetate phthalate 0.035 g cefuroxime axetil 0.6 g | 83.65 | 94.41 | — | — | | |
| 13 | Acid soluble polymer 0.2 g Eudragit S 100 0.1 g cefuroxime axetil 0.6 g | 50.80 | 53.33 | 63.12 | 69.51 | 74.58 | — |
| 14 | Acid soluble polymer 0.3 g Eudragit L 100 0.02 g Cellulose acetate Phthalate 0.02 g cefuroxime axetil 0.6 g | 48.5 | 55.53 | 61.94 | 63.44 | 70.76 | — |

The polymers synthesized in the example 1, 2 and 3, all can be used in the coating compositions for Taste masking The use of polymer synthesized in the example 1 in the various coating compositions disclosed in example 4 is an illustrative example and should not limit the scope of the present invention.

The Advantages of the Present Invention are as Follows:
1. The coating compositions described herein comprising reverse enteric and enteric polymers, do not precipitate as exhibited by the concomitant use of Eudragit E in presence of enteric polymers like Eudragit L and hydroxypropyl methyl cellulose phthalate. The use of acid soluble polymer in presence of enteric polymers like Eudragit L and hydroxypropyl methylcellulose phthalate is not described in any of the earlier works.
2. Though the coating compositions uses the blend of the acid soluble and enteric polymers they can be used for the taste masking applications since the acid soluble polymer remains collapsed or insoluble above the pH 3.5 and hence the coated drug particles can be reconstituted in case of the dry syrup in the pH range of 3.5 to 5.
3. The use of the coating compositions comprising the acid soluble and enteric polymers releases the drug in the acidic pH of the stomach without delay and further the enteric polymer would facilitate the release of any unreleased drug in the intestinal pH. Such coating compositions would therefore provide immediate and also near complete release of the coated drug. Such coating systems would be of use for the drugs, which are absorbed all along the gastrointestinal tract.
4. The incorporation of the pH independent polymers which are not water soluble, along with the acid soluble polymers with or without the enteric polymers, in the coating compositions further aid in the taste masking effect and have the advantage over the systems comprising enteric polymers and pH independent polymers since these do not retard the release of the drug till the transit of the composition to the intestine.
5. The use of the pH independent polymers and acid soluble polymers, which remain collapsed above the pH 3.5, is that they provide with a greater flexibility for the taste masking compositions like dry syrup or suspension compositions which are required to be reconstituted at the pH 3.5 and above unlike the systems incorporating the reverse enteric polymer Eudragit E and pH independent polymers which can be reconstituted at pH 5.5 and above since Eudragit E exhibits swelling up to pH 5.5.
6. The coating compositions use a blend of polymers such that total amount of the polymer is higher enough to taste mask but the amount of individual polymer is low such that it falls within the safe consumable amounts.

We claim:

1. A coating composition for the taste masking of pharmaceutical compositions containing a bitter drug, wherein said coating composition comprises an acid soluble polymer in combination with one or more enteric coating polymers as pH dependent polymer and/or pH independent polymers:
wherein said acid soluble polymer has a formula: $P[A_{(x)} B_{(y)} C_{(z)}]$ wherein P is polymer comprising (A) a hydrophobic monomer, (B) a basic monomer and (C) a hydrophilic monomer and (x)=30-95%, (y)=5-70%, (z)=10-60%, all expressed in terms of w/w such that x+y+z =100%.

2. The coating composition as claimed in claim 1, wherein the acid soluble polymer is comprised of methyl methacrylate, hydroxy ethyl methacrylate and vinyl pyridine in the range of about 50-75%, 15-35% and about 5-15% w/w respectively.

3. The coating composition as claimed in claim 1, wherein a ratio of the acid soluble polymer to the enteric polymer is in the range of 1:0.1 to 1:5.

4. The coating composition as claimed in claim 1, wherein a ratio of the pH dependent polymer to the pH independent polymer is in the range of 1:0.05 to 1:5.

5. The coating composition as claimed in claim 1, wherein a ratio of the acid soluble polymer to the pH independent polymer is in the range of 1:0.1 to 1:5.

6. The coating composition as claimed in claim 1, wherein a blend of pH dependent polymers is used and is selected from the group consisting of a cellulosic ester selected from the group consisting of cellulose acetate phthalate, hydroxymethyl cellulose phthalate, cellulose trimellitate and hydroxymethyl cellulose acetate succinate; a resin selected from the group consisting of shellac and a polymethacrylate selected from the group consisting of copolymers of methylmethacrylate-methacrylic acid, methacrylic acid-ethyl acrylate and polyvinyl acetate phthalate.

7. The coating composition as claimed in claim 1, wherein the pH dependent polymer is used and is selected from the group consisting of a cellulosic ester selected from the group consisting of cellulose acetate phthalate and hydroxymethyl cellulose phthalate, a resin selected from the group consisting of shellac and a polymethacrylate selected from the group consisting of copolymers of methylmethacrylate-methacrylic acid and polyvinyl acetate phthalate.

8. The coating composition as claimed in claim 1, wherein the pH independent polymer comprises a cellulosic ether selected from the group consisting of ethyl cellulose, methyl cellulose, hydroxy ethyl cellulose, hydroxy propyl cellulose, hydroxy propyl methyl cellulose and carboxy methyl cellulose and a protein selected from the group consisting of prolamine and zein.

9. The coating composition as claimed in claim 8, wherein the pH independent polymer comprises a cellulosic ether selected from the group consisting of ethyl cellulose and a protein selected from the group consisting of prolamine and zein.

10. The coating composition as claimed in claim 1 which effectively masks the bitter taste of the drugs.

11. A pharmaceutical composition comprising a coating composition as claimed in claim 1 and a drug, wherein the drug is selected from the group consisting of a macrolide antibiotic selected from the group consisting of erythromycin, azithromycin and clarithromycin; a fluroquinolone selected from the group consisting of ciprofloxacin, enrofloxacin, ofloxacin, gatifloxacin, levofloxacin and norfloxacin a cephalosporin selected from the group consisting of cefuroxime, cephalexin, cephadroxil and cepfodoxime proxetil; a nonsteoroidal, anti-inflammatory and analgesic drug selected from the group consisting of ibuprofen and diclofenac sodium; a COX 2 inhibitor selected from the group consisting of etoricoxib and celecoxib; an antihistamic drug selected from the group consisting of chlorpheniramine maleate; an oxazolidinone selected from the group consisting of linezolid and other drugs selected from the group consisting of dextromethorphan.

12. The pharmaceutical composition as claimed in claim 11, wherein the acid soluble polymer is comprised of methyl methacrylate, hydroxy ethyl methacrylate and vinyl pyridine in the range of about 50-75%, 15-35% and about 5-15% w/w respectively.

13. The pharmaceutical composition as claimed in claim 11, wherein the drug itself or its pharmaceutically acceptable salt or ester or amide is used.

14. The pharmaceutical composition as claimed in claim 11, wherein a ratio of the total polymer to the drug is in the range of 0.5:1 to 3:1 by weight.

15. The pharmaceutical composition as claimed in claim 11, wherein a ratio of the acid soluble polymer to the enteric polymer is in the range of 1:0.1 to 1:5.

16. The pharmaceutical composition as claimed in claim 11, wherein a ratio of the pH dependent polymer to pH independent polymers in the range of 1:0.05 to 1:5.

17. The pharmaceutical composition as claimed in claim 11, wherein a ratio of the acid soluble polymer to the pH independent polymers in the range of 1:0.1 to 1:5.

18. pharmaceutical composition as claimed in claim 11, wherein a blend of pH dependent polymers is used and is selected from the group consisting of a cellulosic ester selected from the group consisting of cellulose acetate phthalate, hydroxymethyl cellulose phthalate, cellulose trimellitate and hydroxymethyl cellulose acetate succinate; a resin selected from the group consisting of shellac and a polymethacrylate selected from the group consisting of copolymers of methylmethacrylate-methacrylic acid, methacrylic acid-ethyl acrylate and polyvinyl acetate phthalate.

19. The pharmaceutical composition as claimed in claim 11, wherein the coating composition consists of the pH dependent polymer selected from the group consisting of a cellulosic ester selected from the group consisting of cellulose acetate phthalate and hydroxymethyl cellulose phthalate, a resin selected from the group consisting of shellac and a polymethacrylate selected from the group consisting of copolymers of methylmethacrylate-methacrylic acid and polyvinyl acetate phthalate.

20. The pharmaceutical composition as claimed in claim 11, wherein the coating composition consists of the pH independent polymer which is comprised of a cellulosic ether selected from the group consisting of ethyl cellulose, methyl cellulose, hydroxy ethyl cellulose, hydroxy propyl cellulose, hydroxy propyl methyl cellulose and carboxy methyl cellulose and a protein selected from the group consisting of prolamine and zein.

21. The pharmaceutical composition as claimed in claim 11, wherein the coating composition comprising the pH independent polymer which is a cellulosic ether selected from the group consisting of ethyl cellulose and a protein selected from the group consisting of prolamine and zein.

22. The pharmaceutical composition as claimed in claim 11, in the form of microparticles wherein the drug is dispersed within polymer matrix or coated by the polymer.

23. The pharmaceutical composition as claimed in claim 22 which, does not release drug at pH of saliva from the oral dosage form but rapidly releases substantial amount of the drug immediately at pH≦3 found in the stomach.

24. The pharmaceutical composition as claimed in claim 11 which is formulated as a syrup or suspension.

25. The pharmaceutical composition as claimed in claim 11 which is formulated in a solid dosage form selected from the group consisting of chewable, effervescent, rapidly disintegrating and dispersible tablets.

26. The pharmaceutical composition as claimed in claim 11 is obtained by dispersion or coating of the bitter drug in the matrix of the coating composition by a technique selected from the group consisting of microencapsulation, spray drying, fluid bed processing, co precipitation in a non solvent and tray drying.

27. The pharmaceutical composition as claimed in claim 11, wherein the taste masked composition is in particulate form, the coating composition comprises a blend of acid soluble polymer and the enteric polymer can be suspended using a reconstitution medium of pH 3.5 to 5.

28. The pharmaceutical composition as claimed in claim 11, wherein the taste masked composition is in particulate form, the coating composition comprises a blend of acid soluble polymer, and The pH independent polymer can be suspended using a reconstitution medium of pH 3.5 to 5.

29. The pharmaceutical composition as claimed in claim 11, wherein the taste masked composition is in particulate form, the coating composition comprises a blend of acid soluble polymer and the pH independent polymer can be suspended using a reconstitution medium of pH>3.5.

30. The pharmaceutical composition as claimed in claim 11, wherein the drug itself or its pharmaceutically acceptable salt or ester or amide is used.

31. The pharmaceutical composition as claimed in claim 11, wherein said composition is prepared by microencapsulation using an emulsification solvent evaporation method comprising dissolving the polymer blend in an organic solvent selected from acetone, methanol, dichloromethane and a mixture of methanol and dicliloromethane in the ratio 1:1 to 1:1.5, or a mixture of acetone and methanol in the ratio 1:1 or a mixture of acetone methanol and dichloromethane in the ratio 1:1:0.1, adding the drug to the polymer solution to obtain a solution or a homogeneous dispersion, adding this organic phase to light liquid paraffin-containing span 85 in an amount of 0.1 to 1% w/w, continuously stirring the mixture mechanically at a rate of about 500 rpm and at a temperature of about 25° C. for a period of about 3-5 hrs and then separating the microparticles by filtration and washing the separated microparticles with petroleum ether or n hexane and drying at a temperature of about 27° C. under vacuum for up to 24 hours.

* * * * *